(12) United States Patent
Holz

(10) Patent No.: US 6,577,704 B1
(45) Date of Patent: Jun. 10, 2003

(54) ANALYSIS DEVICE WHICH USES X-RAY FLUORESCENCE

(75) Inventor: Thomas Holz, Dresden (DE)

(73) Assignee: Fraunhofer-Gesellschaft zur Forderung der angewandten Forschung e.V., Munich (DE)

(*) Notice: Subject to any disclaimer, the term of this patent is extended or adjusted under 35 U.S.C. 154(b) by 0 days.

(21) Appl. No.: 10/019,918
(22) PCT Filed: Jun. 22, 2000
(86) PCT No.: PCT/DE00/02052
§ 371 (c)(1),
(2), (4) Date: Feb. 20, 2002
(87) PCT Pub. No.: WO01/02842
PCT Pub. Date: Jan. 11, 2001

(30) Foreign Application Priority Data

Jul. 6, 1999 (DE) .................................. 199 32 275

(51) Int. Cl.[7] ............................................. G01N 23/223
(52) U.S. Cl. ............................................. 378/44; 378/45
(58) Field of Search .............................. 378/44, 45, 47, 378/49, 68, 70, 73, 84

(56) References Cited

U.S. PATENT DOCUMENTS 5,657,363 A * 8/1997 Hossain et al. ............... 378/45
5,754,620 A * 5/1998 Hossain et al. ............... 378/45

FOREIGN PATENT DOCUMENTS

| DE | 40 15 275 A1 | 11/1991 |
|---|---|---|
| DE | 44 43 853 A1 | 6/1996 |
| EP | 0 456 897 A1 | 11/1991 |
| JP | 09072866 A | 3/1997 |

OTHER PUBLICATIONS

Klockenkämper et al.; "Total–Reflection X–Ray Fluorescence Spectroscopy" *Analytical Chemistry*, 64 (23), 1115a–1123a (Dec. 1, 1992).

Wobrauschek et al.; "TXRF With Synchrotron Radiation Analysis of Ni on Si–Wafer Surfaces," *Nuclear Instruments and Methods in Physics Research*, A363 (3), 619–620 (1995).

* cited by examiner

*Primary Examiner*—Drew A. Dunn
*Assistant Examiner*—Irakli Kiknadze
(74) *Attorney, Agent, or Firm*—Leydig, Voit & Mayer, Ltd.

(57) ABSTRACT

The invention relates to a device for X-ray fluorescence analysis wherein X-radiation of an X-ray source is directed upon a sample arranged on a sample carrier, and the fluorescence radiation is measured by a detector. On that occasion, the detection sensitivity, in particular, with respect to the total reflection X-ray fluorescence (TXRF) is to be increased for the most different samples. In order to solve this problem the sample to be analysed is placed on a multi-layer system, or a fluidic sample flows over such a multi-layer system. The multi-layer system consists of at least two or several individual layers which are arranged in a periodically repeating manner. Adjacent individual layers consist of materials having a different x-ray optical refractive index wherein the period thickness d in the multi-layer system and the angle of incidence $\theta$ of the X-radiation meet the BRAGG relationship at the used wavelength $\lambda$ of X-radiation.

29 Claims, 7 Drawing Sheets

ANALYSIS DEVICE WHICH USES X-RAY FLUORESCENCE

The invention relates to an X-ray fluorescence analysis device and to a method for carrying out such analyses and the use of this device. In particular, the device is appropriate to the trace element analysis, and comprises possible application fields, particularly both in the environmental analysis and thin film technology (semiconductor technology).

The highest detection sensitivity with the X-ray fluorescence analysis one achieves in that X-radiation having an angle of incidence at which total reflection occurs is directed upon a sample on a sample carrier wherein the angle of incidence has to be lower than the critical angle $\theta_c$ of the total reflection which is caused by the matter properties of the sample carrier material. The critical angle $\theta_c$ results from the refractive index (n=1−δ+iβ; 1−δ→real part [dispersion], iβ→imaginary part [absorption] of the sample carrier material with $\theta_c=\sqrt{2\delta}$ ($\theta_c$ [rad] as an radian measure). The greater is the photon energy of the used radiation the lower is the critical angle $\theta_c$, and being approximately 0.1° with e.g. Mo K type irradiation for a quartz carrier. However, the lower is the angle of incidence $\theta_c$ the greater is the projection of the primary beam section upon the sample carrier. Therefore, the sensitivity of detection (related to the number of atoms to be detected per surface) of the total reflection X-ray fluorescence analysis (TXRF) is essentially limited by the obtained photon flux density of the exciting primary radiation per surface unit.

Increasing the photon flux density of the X-radiation by means of focussing polychromatic or monochromatic radiation is possible but does not merely have any practical significance due to the small angles $\theta_c$.

With the total reflection the radiation portion refracted within the sample carrier is degraded toward the surface wave exponentially fading into the depth, and the penetrating depth (several nanometers only, int. al. <10 nm) of the X-radiation into the sample is controlled in a dispersive manner. Typically, more than 95% of the incident radiation will be reflected.

By the limitation of the sample carrier volume excited with the sample to a few nanometers a very high signal-to-background ratio is to be written down. The portions of the background generated in this area in the vicinity of the surface are reaching the detector in an unattenuated form, however, and will be consequently measured therewith.

A measuring arrangement based on this findings is described in EP 0 456 897 A1. There, an X-ray source is used wherein the X-radiation thereof is directed upon a sample carrier by means of at least one reflecting unit under the conditions of total reflection. The fluorescence radiation thus excited is measured by a detector, and the sample is respectively analysed. A second detector senses the X-radiation reflected on the sample carrier, and the control of the critical angle of the total reflection is allowed to be readjusted by means of an angle resolved type measurement with respective handling the reflector unit and the sample carrier.

The respective sample is immediately placed on the sample carrier. A periodically repeating sequence of one or more layers made of materials having a different refractive index is formed on the reflector unit. On that occasion, layers are mentioned wherein having such a pair of layers, at least one layer is relatively large-atomic. Thus, so called multi-layer mirrors are used to diffract the X-radiation on the reflector unit. However, the fluorescence excitation exclusively occurs under the conditions of the total reflection on the sample carrier in acceptance of the mentioned and well known drawbacks.

Therefore, it is an object of the invention to increase the detection sensitivity of most different samples.

This object preferably is achieved by the characterizing features of the present invention. Advantageous embodiments and further developments of the solution will be apparent from the description of the invention provided herein.

With the device according to the invention the radiation from an X-ray source for the fluorescence excitation of a sample which can be solid or fluidic is directed upon a multi-layer system serving as a sample carrier. The multi-layer system comprises a number of at least two layers which are made of materials having a different x-ray optical refractive index, respectively. The period thickness d of one period meets the BRAGG relationship in consideration of the incident angle $\theta_{in}$ of radiation with λ upon the surface of the multi-layer system. The period thickness d and the sequence of individual layers is allowed to be constant for the respective adjacent periods in the multi-layer system wherein in this case it is allowed to be said of periodically built-up multi-layer systems.

In addition, there is also the way to modify the structure of the multi-layer system by changing one or several individual layer thicknesses such that in contrast to the periodical structure a higher reflectivity and/or a lower angular acceptance is achieved with the predetermined $\theta_m$ and wavelength λ of the incident X-radiation photons. In this case it is being said of a periodically constructed multi-layer systems.

With the use of one or several reflector unit(s) it has to be taken account of the period thickness $d_j$ of each surface element $A_j$ of the multi-layer system on a reflector unit which has to be selected such that the X-radiation photons reflected from this multi-layer system and directed upon the multi-layer system arranged on the sample carrier meet the BRAGG relationship in the sample location. On that occasion, influencing the angle of incidence of the radiation can take place by moving the sample carrier and/or with at least one reflector unit which is arranged in the optical path between the X-ray source and the surface of the multi-layer system.

The radiation is allowed to be directed upon the used multi-layer system on the sample carrier in consideration of the BRAGG relationship $$m^*\lambda = 2d_{eff}^*\sin\theta_m$$

wherein
m is a whole number 1, 2, 3 . . .

$$d_{eff} = d\left(1 - \frac{\overline{\delta}}{\sin^2\theta_m}\right)$$

wherein
d is a period thickness of the multi-layer system, and $$\overline{\delta} = \frac{1}{d}\sum_{i=1}^{m} d_i \delta_i$$

is a mean value weighed according to the thickness of the real parts of the refractive index of all layers of one period, with an angle of incidence being substantially greater than it is the case with the total reflection. On that occasion, the photon flux density/surface element of the exciting X-radiation can be greater by the factor $\sin\theta_m/\sin\theta_c$ as it is the case with the total reflection as the reflected radiation portion is in the same procentual range as with the total reflection. Herein, $\theta_m$ is the BRAGG angle of the $m^{th}$ maximum which is greater than the critical angle θ of total reflection, and which is substantially determined by the period thickness d of the layer pairs of the multi-layer system, and which is not determined by the δ-values of the layers.

The highest reflectivities of multi-layer systems can be found within the first order (m=1).

Depending on the amount of reflectivity a continuous wave field is forming on the surface of the multi-layer system arranged on the sample carrier which can be employed for the fluorescence excitation of the sample. With an appropriate choice of the period number, period thickness and layer materials in the multi-layer system reflectivities can be achieved which almost are corresponding to those with total reflection(R>90%).

The mulitlayer system is allowed to be formed on a substrate, e.g., with well known methods of thin-film technology (plasma enhanced chemical vapour deposition PLD, chemical vapour deposition technique CVD, sputtering or other). The individual layers and the substrate should be composed of elements and compounds of elements having the atomic numbers of Z<10, respectively. The fluorescent lines of the layer materials and substrate materials, as is the case, thereby are not located within the power interval of the elements to be detected in the sample, and they do not contribute to the background. Thereby, elements having greater atomic numbers can be detected with a higher detection sensitivity.

Appropriate elements include H, B, Be, Li, N and C and the compounds $B_4C$ and $CN_x$ as well. Favourably, the various modifications of carbon such as diamond-like or graphite-like carbon can also be used in a pair of layers. Organic compounds consisting of C, N, O and H are conceivable as well.

Glassy carbon is an appropriate substrate material whereon a respective multi-layer system can be formed. Glassy carbon is commercially availabe, e.g. with the indication of "Sigradur".

It is also advantageous to use such a multi-layer system for beam forming and/or for the monochromatization on at least one reflector unit thus the fluorescent lines of the reflector unit(s) are not located within the energy interval to be detected.

In contrast to the conventional total reflection X-ray analysis, it is possible with the invention to increase the photon flux density of the exciting X-radiation several times without deteriorating the signal-to-background ratio. In addition, more effecient focussing of polychromatic X-radiation is allowed wherein in the following it will be noted yet to possible implementations therewith. With focussing it should be considered that each photon meets the BRAGG condition in the impact point upon the multi-layer system. This can be implemented if the wavelength of the incident photons increases according to the BRAGG relationship with the angle of incidence thus occurring a direction dependent monochromatization of each partial beam.

Complying this condition, with a reflector unit it is allowed to focus upon the surface of the multi-layer system arranged on the substrate carrier a polychromatic exciting radiation having an aperture angle of the convergent radiation which is several times greater than the angle of incidence for total reflection.

By means of an elliptically curved gradient layer system upon at least one reflector unit a divergent polychromatic X-radiation is thus allowed to be converted into such a polychromatic, i.e. direction dependent monochromatic radiation which can be focussed according to the reflection conditions upon the surface of the multi-layer system arranged on the sample carrier.

In an analogous manner parallel polychromatic radiation can be focussed upon a sample by means of parabolically curved gradient multi-layer systems.

For focussing the X-radiation upon a mulitlayer system arranged on the sample carrier one mulitlayer system of a reflector unit having the form of a equiangular spiral can also be used.

If the radiation is not focussed upon the multi-layer system arranged on the sample carrier thus the BRAGG relationship means that monochromatic parallel radiation has to be incident.

By means of a respective parabolically curved multi-layer system which period thicknesses d of the layer pairs thereof are selected as gradients of period thickness, a divergent polychromatic X-radiation is allowed to be converted into a monochromatic parallel radiation wherein the period thickness depression in the multi-layer system on a reflector unit ensures that the X-radiation photons impacting upon the multi-layer system arranged on a sample carrier meet the BRAGG relationship.

Parallel polychromatic radiation can be converted into a monochromatic parallel radiation by means of a plane multi-layer system having a constant period thickness d.

For simultaneous proofing the fluorescence radiation of different elements an energy dispersive detector can be used for the detection of fluorescence.

Advantageously, the detector is to be cooled for energy dissolving wherein a Peltier cooled detector having a Lithium Peltier element or liquid nitrogen can be used.

In addition, it is possible to place poly-capillary optics between the detector and multi-layer system arranged on the sample carrier to enable a locally resolved type measurement. On that occasion, the focus of the poly-capillary optics is set toward the sample by means of an elevation adjustment.

For different applications it is favourable to moderate the sample carrier. Thus, solid and liquid samples, respectively, are allowed to be vaporized by warming, and the fluorescence analysis can be carried out thereafter, if required.

However, for particular samples and analyses, respectively, cooling can make sense as well.

Synchrotrons, rotating anodes or X-ray tubes as well can be used as the X-ray sources. On that occasion, merely the various radiation divergences (e.g. micro focus type tubes or fine focus type tubes), and wavelengths in particular with the layout of the multi-layer system(s) are to be taken into account. The modular structure of the measuring arrangement ensures the simple adaptation to the various X-ray sources.

It is also advantageous to monitor complying the BRAGG angle and the BRAGG maximum by means of a second detector. This detector measures the intensity of reflected radiation of the multi-layer system arranged on the surface of the sample carrier. On that occasion, sensibly a locally resolved type measurement occurs, e.g. with the line shaped detector or with a detector array. According to the radiation sensitivity measured the beam guidance and the incident angle of the exciting radiation upon the surface of the multi-layer system can correspondingly be varied here such that the maximum intensity will be measured. Herewith, the position of the multi-layer system on the sample carrier with respect to the incident X-radiation can be adapted, e.g. by horizontal and/or vertical shifting or by pivoting about a horizontal axis in order to measure within the optical range.

However, a respective influence can also be achieved solely or in addition to respective motions on the reflector unit(s). In each case, however, a positioning way is desirable in at least one degree of freedom for the sample carrier and/or the reflector unit.

If several reflector units are subsequently arranged in the optical path of the exciting radiation, the beam direction is allowed to be influenced in a most different manner according to the number and angular orientation.

This invention can be advantageously used with environmental analysis, and here, in particular, with proofing the minimum concentrations of toxic and other matters, respectively.

Another application would be the online type inspection of vacuum deposition methods wherein the deposition atmosphere can be monitored.

In the semiconductor technology/microelectronics the demands relating the chemical purity of wafers continuously increase. Consequently, the detection sensitivity has to be enhanced as well. This is enabled by combining the well known VPD method with the invention and lowering the detection limit which is thus achievable.

As already mentioned samples of most different phase can be analysed.

(a) However, with respect to fluids it is significant to guide them in accordance with specific flow conditions into and over the analyzing area, respectively, on the surface of the multi-layer system arranged on the sample carrier.

(b) Thus, particle shaped samples are allowed to be analysed on a multi-layer system.

(c) A liquid sample can be gained, e.g. by means of VPD (Vapour phase deposition) from a Si wafer, or such as e.g. sea water it can be extracted directly from the environment.

The device comprising its various elements can be formed in a closed housing. In the housing the respective analysis can be carried out in a vaccum. However, detecting is also possible within an inert nitrogen atmosphere or helium atmosphere or other gas atmospheres (Z<10) if the fluorescence, e.g., of argon contained in the air largely contributes to the background.

In the following the invention shall be explained by way of example.

In the drawings

FIG. 1 shows the diagrammatic structure of an example of the device according to the invention;

FIGS. 2a–d show graphical representations of the reflectance being dependent on the angle of incidence;

Figure 1:
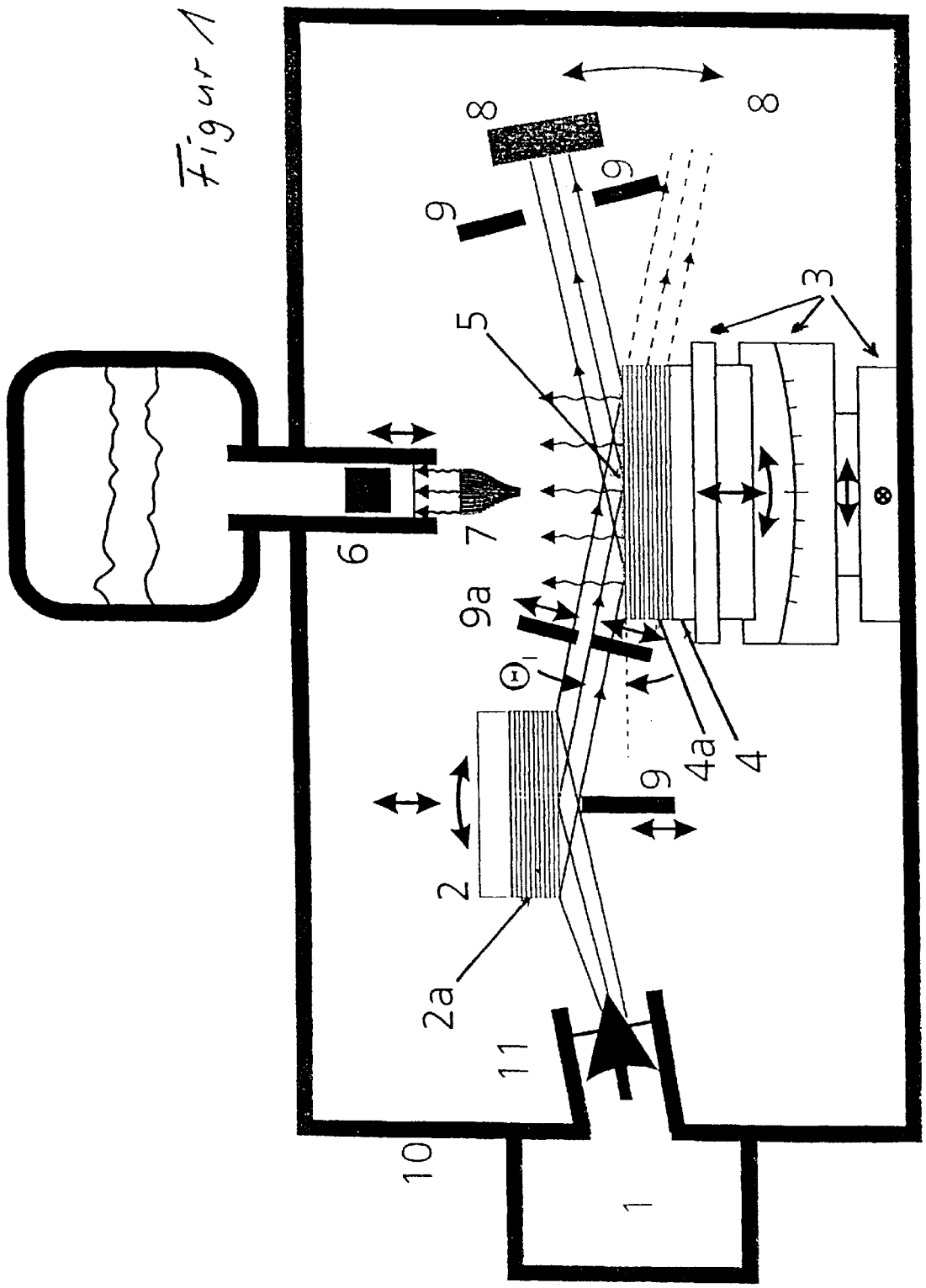

In FIG. 1 is diagrammatically shown an embodiment of the device according to the invention. On that occasion, an X-ray source 1 is flanged to a housing 1, and through a beam entering aperture 11 with and without a window, respectively, X-radiation is directed upon a reflector unit 2 on which reflecting surface thereof is formed a multi-layer system 2a which meets the conditions as mentioned in the general part of the description. A window at the beam entering aperture 11 is required during working in the vacuum. The radiation from the surface of the multi-layer system 2a is directed upon a second multi-layer system 4a which is arranged here on a sample carrier 4, and is partially reflected from the surface of the multi-layer system 4a. The sample 5 is located on the multi-layer system 4a.

Complying the BRAGG conditions (period thickness d in the layer stack and a respective angle of incidence $\theta_m$ thereof, preferably m=1) a standing X-radiation wave field is forming which has a relative high intensity above the surface of the multi-layer system 4a, and fluorescence is excited in a sample 5 which is placed there. The fluorescence is measured with the detector 6 preferably in a energy dispersive manner. The detector 6 is cooled from the outside as it is diagrammatically outlined.

Poly-capillary optics 7 can optionally be inserted between the layer stack 4a and detector 6.

For beam limitation a plurality of shutters 9 are available.

The shutter 9a, which the position and slit width thereof can be varied, is allowed to stop away from the beam reflected from the multi-layer system 2a portions for the excitation of the sample. This shutter 9a can be shifted in translational manner, e.g. at least along one axis. By means of the shutter 9a a defined partial interval of wavelength of a polychromatic radiation focussed from the multi-layer system 2a of the reflector unit 2 can be stopped away.

With this example a second detector 8 is available wherein complying the BRAGG condition can be monitored. Depending on the radiation intensity measured by the second detector the angle of incidence $\theta_m$ can be readjusted, preferably with m=1.

A respective influence of the angle of incident $\theta_m$ can be achieved by means of respective motions of the reflector unit 2 and/or the sample carrier 4, with a manipulator 3 wherein translational or pivoting motions as well are possible as indicated with the various double arrows.

Figure 2:
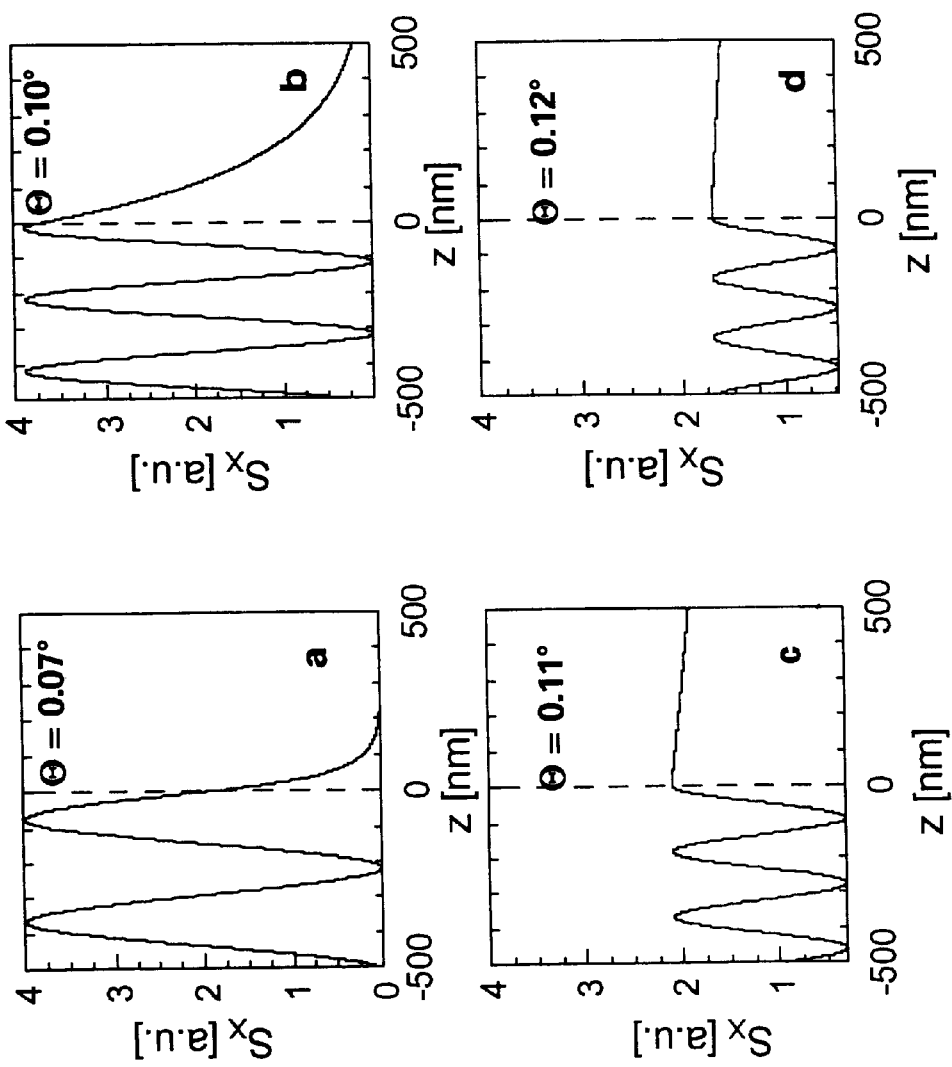
Figure 3:
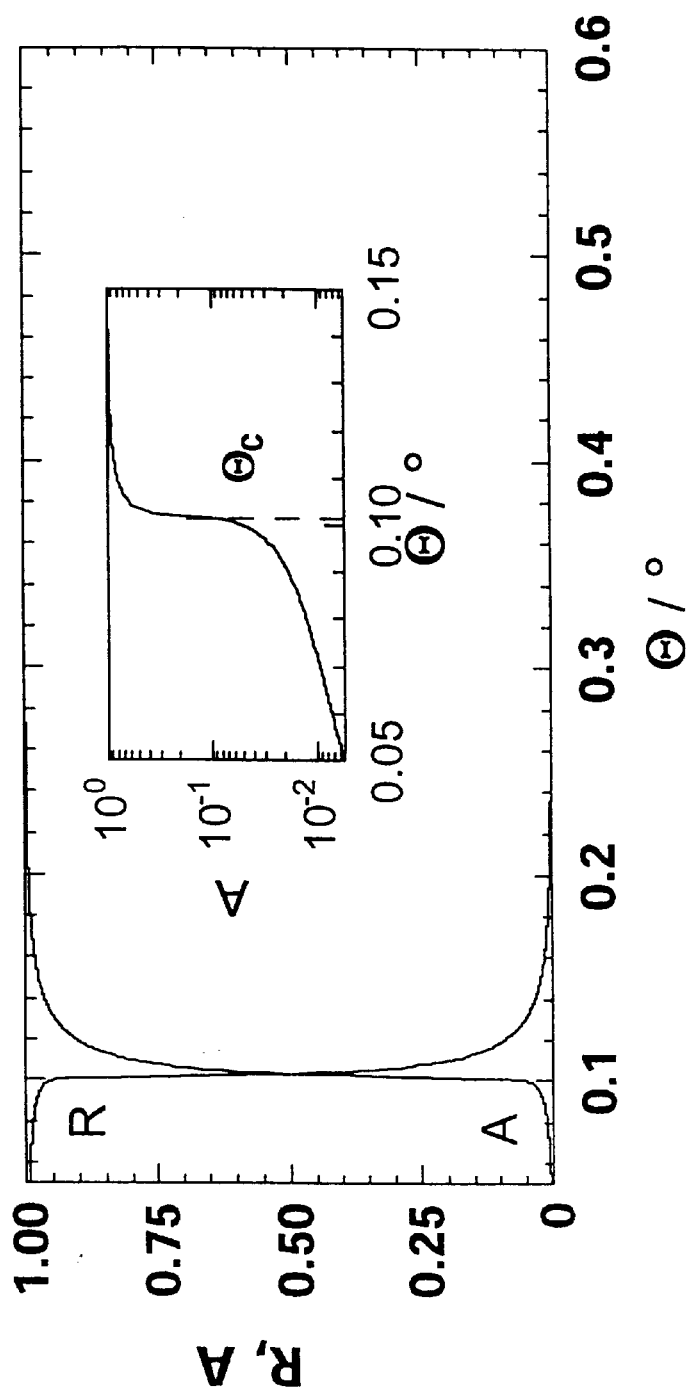
FIG. 3 shows a diagram of the reflected and absorbed portion of radiation in the silicon.

The FIGS. 2 and 3 characterize the TXRF method determining the prior art in more detail.

The graphical representations shown in the FIGS. 2a to 2d illustrate that depending on the reflectivity dependent on the incident angle of a surface a standing wave field being developed in a more or less strong manner is forming above a surface. It can be locally achieved the four times intensity of the employed primary radiation. The ratios $S_x=f(z)$ are considered with angles of incidence being below the critical angle of the total reflection in the FIGS. 2a and 2b, and with $\theta>\theta_c$ angles of incidence being greater than the critical angle $\theta_c$ in the FIGS. 2c and 2d having a silicon surface and MoK type α-primary radiation.

The reflected and absorbed radiation portions on/within the silicon which in a first approximation are adding to 100% can be gathered from the diagram depicted in FIG. 3. In the inset is illustrated the absorbed portion dependent on the angle of incidence. This is about 5% in the vicinity of $\theta_c$. This portion forms together with the radiation portion of the primary radiation dispersed on a sample the background in the measured signal according to the selection of the operating point.

The FIGS. 2a to 2d and 3 should make clear how in the TXRF the very good signal-to-background ratio comes into being, and why this method is limited to $\theta<\theta_c$. The FIGS. 4 to 6 should illustrate why a similarly good signal-to-background ratio is allowed to originate in the BRAGG angle of $\theta_{m=1}$ on the basis of another physical principle.

Figure 5:
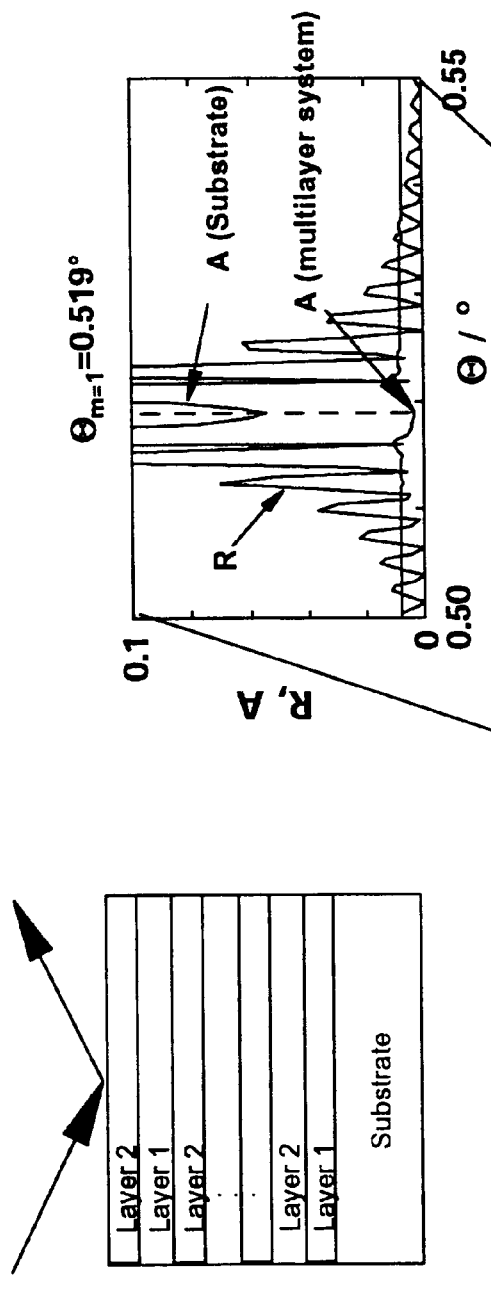
FIG. 5 shows a diagram of the absorbed portion of radiation minimized in the BRAGG maximum.
Figure 4:
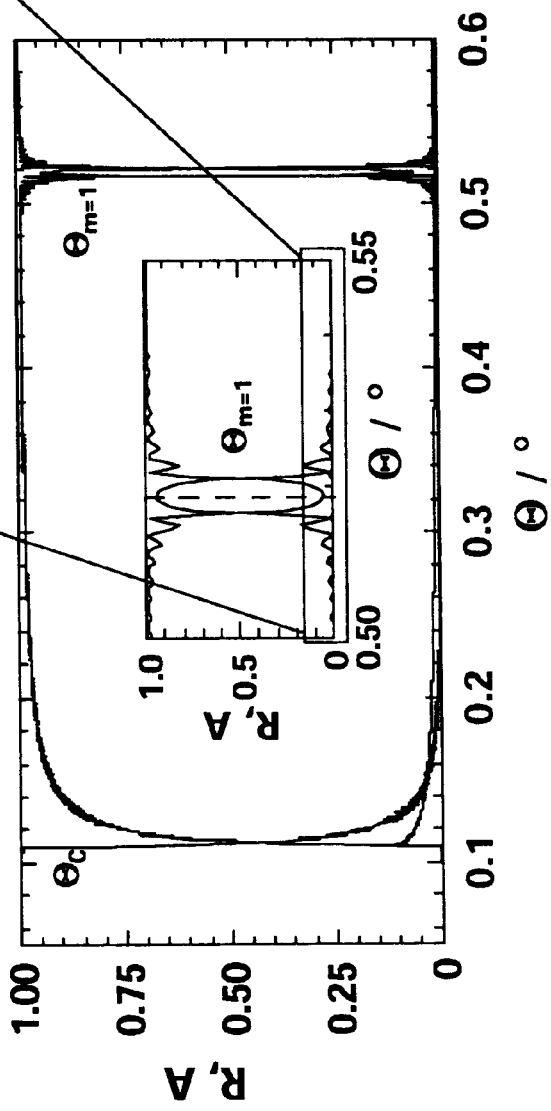
FIG. 4 shows a diagram of the reflected and absorbed portion of radiation with a multi-layer system having C/C layers arranged in an alternating manner.
Figure 6:
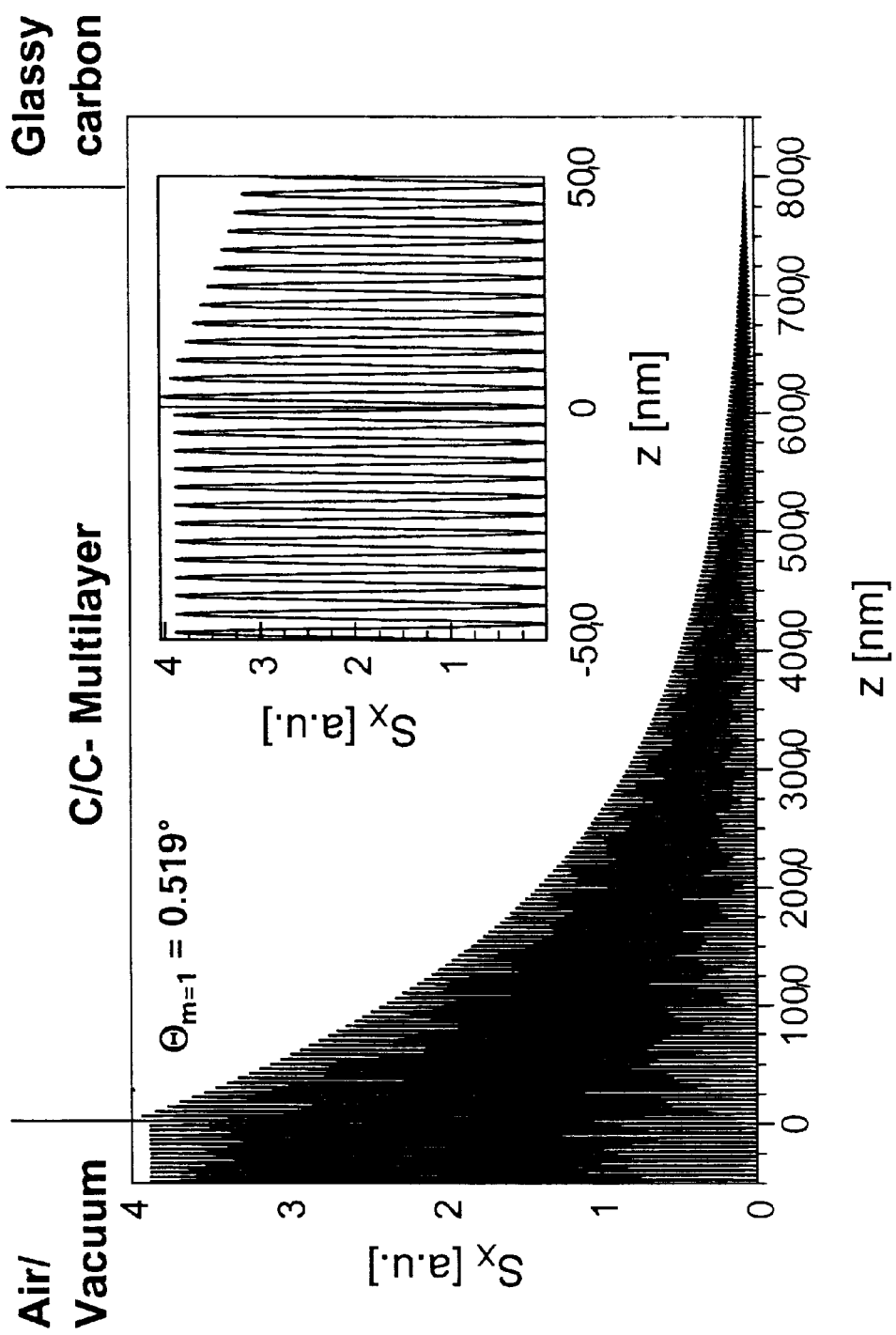
FIG. 6 shows the intensity of a standing wave field originating from above the surface of a C/C multi-layer system up into the multi-layer system.

In the FIGS. 4 to 6 the various calculated ratios can be gathered for a multi-layer system having individual layers alternately composed of diamond like and graphite like carbon which is formed on a glassy carbon substrate.

One C/C multi-layer system has been considered with 200 pairs of layers and with a period thickness of d=4 nm. The graphite like carbon layers have a density of 2.2 g/cm³, and the diamond like carbon layers have a density of 3.5 g/cm³. Therefrom results a sufficient radiographically optical contrast between the two modifications of carbon.

The reflected portions being absorbed in the multi-layer system of the primary radiation used for the excitation can be gathered from the diagram according to FIG. 4. It can be seen that within the range of total reflection the relations are corresponding to those which can be gathered from the FIGS. 2a–d and FIG. 3. Outside the range of total reflection respective reflectivities are to be recorded only in the vicinity of the BRAGG maximum as it is illustrated in the inset. The portion absorbed in the substrate comprises its smallest value in the reflectivity maximum. This also relates to the portion absorbed in the multi-layer system (FIG. 5).

The portion which is absorbed in the substrate (appr. 5%) is allowed to produce a scattered radiation. However, this passes to the detector only after the passage through the multi-layer system. With complying the BRAGG conditions less than 1% will be absorbed.

With the FIG. 6 the formation of the standing wave field is made clear as the course of $S_x=f(z)$. The wave field does not form itself above the surface of the multi-layer system but in its interior as well. On that occasion, a decrease of intensity with an increasing depth in the multi-layer system is recognisable.

The period of the wave field corresponds to the period thickness d of the multi-layer system. Due to the formation of a standing wave field the component of the Poynting factor $S_x$ (z) running parallel to the surface achieves locally values which are four times greater than the primary radiation used for the excitation of fluorescence.

For the excitation of fluorescence in the sample a monochromatic parallel radiation can be used and thus a greater surface area can be detected.

Herein, on the one hand, a respective parallel polychromatic radiation (e.g. synchrotron radiation) can be used which is directed upon a plane multi-layer system having a constant period thickness d. But on the other hand, a divergent polychromatic radiation is allowed to be converted into a monochromatic parallel radiation with a parabolically curved multi-layer system. This multi-layer system is formed as a gradient layer system, i.e. the layer thickness of the indiviual layers and therefore the period thickness d as well is not constant but it does continuously increase from one side of the multi-layer system to the other, namely, such that in each surface element on the parabolically curved surface the BRAGG conditon is met, and the maximum intensity in the parallel beam is to be found.

On the sample carrier in the location of the sample it is considered to be that $$\lambda = 2d\sqrt{\sin^2\theta_{m-1} - 2\bar{\delta}}$$

wherein $\bar{\delta}$ is derived from the mean value of the $\delta$ values weighed according to the layer thickness of all layers of a multi-layer system (formed real part of the refractive index of all layers);

$\lambda$ is the wave length of X-radiation;

$\theta_{m=1}$ is the angular position BRAGG peak of the first order, wherein the parabolically curved reflector unit 2 creates a parallel radiation of the wavelength $\lambda$ exactly when on each surface element of the multi-layer system 2a it is considered to be:

$$d_{\delta Aj} = \frac{\lambda}{2\sqrt{\sin^2\theta(Aj) - (2\bar{\delta})_{Aj}}}$$

wherein $\theta$ (Aj) can be derived from the distance of the surface element from the parabolic parameter p and the distance from the focal point.

$$Y = \sqrt{2px}$$

Figure 7:
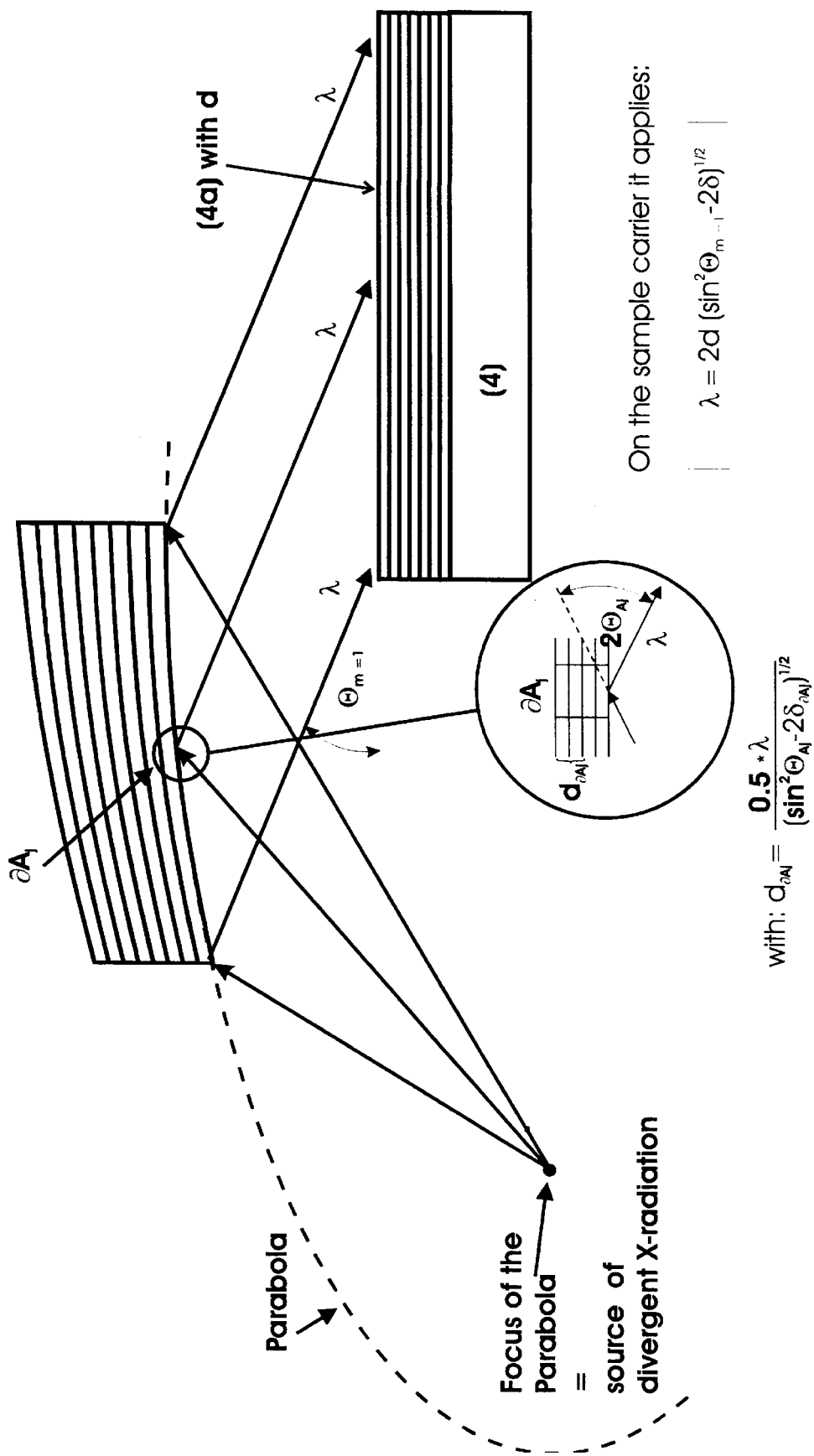
FIG. 7 shows a diagrammatic illustration how a divergent X-radiation is allowed to be converted into a parallel monochromatic radiation.

These facts are diagrammatically shown in FIG. 7. For such a radiation conversion at least one reflector unit can be appropriately formed and be used.

Figure 8:
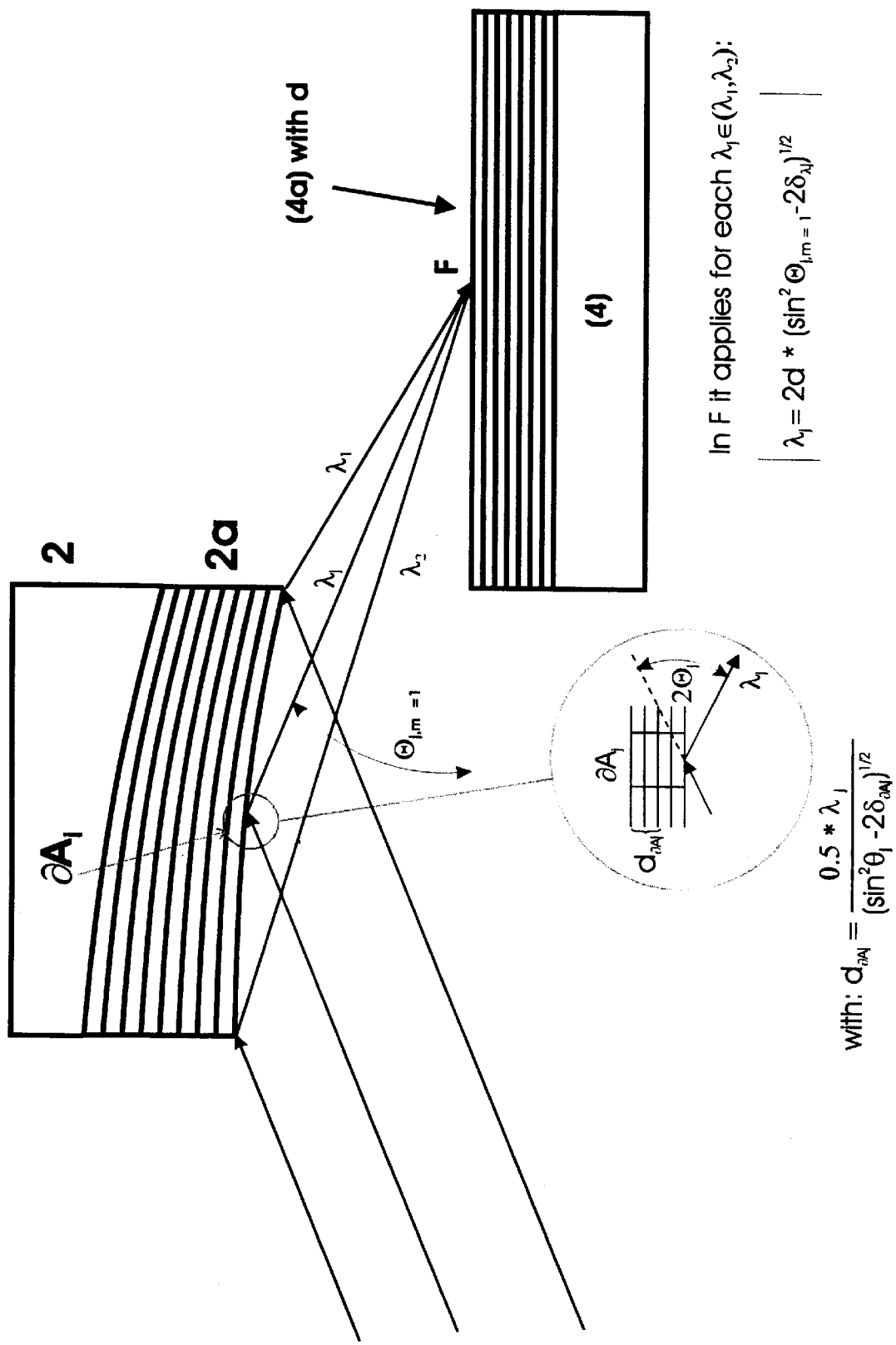
FIG. 8 shows a diagrammatic illustration how a parallel X-radiation can be focussed upon a surface.

As shown in FIG. 8 it is also allowed to focus polychromatic radiation upon a surface for the detection of a sample.

For this, a gradient layer system curved parabolically (for a parallel beam) or curved elliptically (for a divergent beam) can be used. On that occasion, the partial monochromatization of a $j^{th}$ surface element on the multi-layer system 2a has to be such that the photons having the wavelength $\lambda_j$ reflected on the multi-layer system 4a is matched with the angle of incidence $\theta_{jm=1}$ to the period thickness d of the multi-layer system 4a such that the BRAGG relationship is valid for each exctiting X-radiation photon on the surface.

For all $\lambda_j \epsilon (\lambda_1, \lambda_2)$ in the impact point F on the multi-layer system 4a it is considered to be $$\lambda_i = 2d^* \sqrt{\sin^2\theta_{j,m-1} - 2\bar{\delta}\lambda i}$$

wherein $\bar{\delta}$ ($\lambda_i$) is a wavelength depending mean $\bar{\delta}$ weighed according to the layer thickness determined from the $\delta$ values of all layers) which is the function of the wavelength, mean real part of the refractive index of all layers at $\lambda_i$.

What is claimed is:

1. A device for the X-ray fluorescence analysis wherein an X-ray source directs X-radiation upon a sample located on a sample carrier, and a detector is available for the detection of the fluorescence radiation characterized in that said sample is placed on a multi-layer system, or that a fluidic sample flows over said multi-layer system, wherein said multi-layer system is formed of at least two or more individual layers which are arranged in a periodically repeating manner, and adjacent individual layers are composed of materials having different x-ray optical refractive index; and the period thicknesses d in the multi-layer system and the incident angle $\theta$ of the x-radiation meet the BRAGG relationship with the used wavelength $\lambda$ of X-radiation.

2. A device according to claim 1 wherein said multi-layer system is formed on said sample carrier or on a substrate.

3. A device according to claim 1 wherein said individual layers and said substrate are composed of elements having an atomic number Z<10, or of compounds of these elements.

4. A device according to claim 1, wherein at least one reflector unit is arranged between said X-ray source and said multi-layer system in the optical path of the X-radiation.

5. A device according to claim 1, wherein a multi-layer system consisting of at least two individual layers or a plurality of individual layers arranged in a periodically repeating manner is arranged on the reflector unit(s), and in that adjacently arranged individual layers respectively have different x-ray optical refractive indices.

6. A device according to claim 1, wherein said period thickness d of the individual pairs of layers of a multi-layer system are within the range of 1 nm to 20 nm.

7. A device according to claim 1, wherein the individual layers consist of $B_4C$, BN, $CN_x$, B, Be, Li or of various modification of the carbon or organic compounds with C, H, N and O.

8. A device according to claim 2, wherein said substrate consists of glassy carbon.

9. A device according to claim 1, wherein an energy dispersive detector is available for the detection of fluorescence radiation.

10. A device according to claim 1, wherein a polycapillary optics is arranged between said detector and said multi-layer system comprising a sample for a locally resolved type measurement of fluorescence radiation.

11. A device according to claim 1, wherein said sample carrier can be moderated.

12. A device according to claim 1, wherein a second detector is available for measuring the intensity of the X-radiation reflected on the surface of said multi-layer system.

13. A device according to claim 1, wherein said sample carrier having said multi-layer system and/or reflector unit(s) is/are movable and/or pivotable in the translational direction with at least one degree of freedom.

14. A device according to claim 1, wherein the elements are received in a sealed housing which can be evacuated or filled with an inert gas.

15. A device according to claim 1, wherein said detector for measuring the fluorescence radiation is cooled.

16. A device according to claim 15 wherein said detector is Peltier cooled.

17. A device according to claim 1, wherein said X-ray source is a synchrotron, a rotating anode or an X-ray tube.

18. A device according to claim 1, wherein at least one shutter which can be moved in the translational direction is arranged within the optical path of the X-radiation between said X-ray source and the sample.

19. A method for performing X-ray fluorescence analysis with a device according to claim 1, wherein the X-rays of said X-ray source will be directed with an incident angle $\theta_m$ considering the x-ray optical characteristics of said multi-layer system upon the surface of said multi-layer system arranged on the surface of said sample carrier which ensures the BRAGG reflection of the incident X-ray photons.

20. A method according to claim 19 wherein said sample carrier having said multi-layer system, and/or said reflector unit(s) are shifted in the translational direction and/or pivoted about an axis in consideration of the intensity of the X-radiation reflected on the surface of said multi-layer system which is measured with the second detector.

21. A method according to claim 19 wherein a divergent polychromatic radiation is converted into a monochromatic parallel radiation by means of a parabolic curved multi-layer system which gradients of layer thickness thereof are matched to its curvature.

22. A method according to claim 19 wherein a parallel polychromatic radiation is converted into a parallel monochromatic radiation by means of said plane multi-layer system having a constant period thickness d.

23. A method according to claim 19 wherein a divergent X-radiation is focussed by means of a parabolically, elliptically or logarithmic spiral shaped curved gradient layer system upon the surface of said multi-layer system arranged on said sample carrier wherein the distribution of period thicknesses of said multi-layer system on the reflector unit ensures that the X-radiation photons directed upon said multi-layer system meet the BRAGG conditions.

24. A method according to claim 19, wherein a liquid sample vaporizes on said sample carrier and will be analysed.

25. A method according to claim 19, wherein a gaseous sample is guided over the surface of said multi-layer system.

26. A method according to claim 19, wherein a partial interval of a polychromatic X-radiation focussed upon said multi-layer system is stopped away with said shutter.

27. Use of a device according to claim 1 in the environmental analytics.

28. Use of a device according to claim 19, wherein a particle shaped sample is used.

29. Use of a device according to claim 1, wherein a liquid sample is used which has been taken from a Si wafer by means of VPD.

* * * * *